United States Patent [19]
Kogan et al.

[11] Patent Number: 4,910,205
[45] Date of Patent: Mar. 20, 1990

[54] TRANSDERMAL DELIVERY OF LORATADINE

[75] Inventors: Patricia W. Kogan, Union, N.J.; Joel A. Sequeira, New York, N.Y.

[73] Assignee: Schering Corporation, Kenilworth, N.J.

[21] Appl. No.: 188,922

[22] Filed: May 2, 1988

[51] Int. Cl.$^4$ ................................................ A61K 9/70
[52] U.S. Cl. .................................... 514/290; 424/447; 424/448; 424/449
[58] Field of Search ...................... 424/447, 448, 449; 514/290

[56] References Cited

U.S. PATENT DOCUMENTS 4,560,553 12/1985 Zupan ..................................... 424/78
4,659,716 4/1987 Villani et al. ........................ 514/290

Primary Examiner—Ellis P. Robinson
Assistant Examiner—Leon R. Horne
Attorney, Agent, or Firm—Anita W. Magatti; John J. Maitner; Stephen I. Miller

[57] ABSTRACT

A pharmaceutical composition for the transdermal delivery of loratadine comprising isopropyl myristate and rosemary oil and the method of using such a composition for the treatment of allergic reactions are disclosed.

12 Claims, No Drawings

TRANSDERMAL DELIVERY OF LORATADINE

The present invention relates to a pharmaceutical composition for transdermal delivery of the antihistamine loratadine or its decarbalkoxylation product, and to a method of using such a composition in the treatment of allergies.

In particular, the pharmaceutical composition comprises loratadine or its decarbalkoxylation product, a pharmaceutically acceptable volatile solvent, preferably ethanol, an essential oil, preferably rosemary oil, and a fatty acid ester, preferably isopropyl myristate.

Loratadine, the USAN chemical name of which is ethyl 4-(8-chloro-5,6-dihydro-11H-benzo[5,6]cyclohepta [1,2-b]-pyridin-11-ylidene)-1-piperadine-carboxylate is an antihistamine which is water insoluble and which penetrates human skin poorly. Loratadine is claimed in U.S. Pat. No. 4,282,233. The antihistaminic decarbalkoxylation product of loratadine, 8-chloro-6,11-dihydro-11-(4-piperidylidene)-5H-benzo[5,6]cyclohepta [1,2-b]-pyridine, also water insoluble and a poor penetrator of human skin, is claimed in U.S. Pat. No. 4,659,716. Hereinafter, unless otherwise indicated, in the specification the term "loratadine" refers to both loratadine and its decarbalkoxylation product.

The present invention provides a transdermal delivery system for the administration of loratadine and more specifically provides a method and a composition wherein a transdermal device, especially a reservoir patch, is conveniently applied to the skin to provide transdermal loratadine administration over a prolonged period of time. Thus, the method, composition and patch of the invention can be used to provide systemic treatment remote to the site of application, i.e., the antihistamine activity can be provided by distribution of loratadine via the blood rather than by local antihistamine activity at the site of application of the loratadine transdermal composition and/or patch.

The use of transdermal drug delivery systems produces more controlled blood levels, lower frequency of dosing and enhanced patient compliance. Further, the transdermal delivery of an antihistamine to treat various allergic reactions is most desirable for reasons of convenience and effectiveness.

The invention sought to be patented in its method aspect is a pharmaceutical method for the systemic treatment of allergic reactions in a mammal which comprises the transdermal application of an effective amount of loratadine and a pharmaceutically acceptable transdermal carrier. The preferred mode for accomplishing the transdermal application of loratadine is via a transdermal patch.

We have surprisingly found that a combination of a volatile solvent, an essential oil and a fatty acid ester produces a transdermal flux of loratadine greater than the transdermal flux in the volatile solvent alone, in the volatile solvent and the essential oil, or in the volatile solvent and the fatty acid ester.

Essential oils are volatile oils that impart the characteristic odors to plants and are most commonly used in perfumes or as flavoring agents, although several oils, e.g. wintergreen (methyl salicylate) and peppermint (principally menthol) oils are used for pharmaceutical purposes, e.g. as counterirritants or local anesthetics. In EP No. 70,525, peppermint and wintergreen oils were disclosed to act as solubilizing agents in pharmaceutical compositions for administering miconazole and other antifungal agents. Essential oils useful in the present invention include eucalyptus, spearmint, cedarwood, wintergreen, peppermint and rosemary oils, with rosemary oil being preferred.

Lipoidal solvents such as fatty acid esters are widely used in the pharmaceutical and cosmetic industries as emollients. Isopropyl myristate is preferred for use in the instant invention since it is known as an especially effective absorption enhancer due to its similarity to skin. Other fatty acid esters useful in the present invention are isopropyl stearate, isopropyl palmitate, isopropyl isostearate, or combinations of the named esters.

Pharmaceutically acceptable volatile solvents include pharmaceutically acceptable lower alcohols such as methanol, isopropanol and ethanol, and volatile silicone fluids such as cyclomethicone, with ethanol being preferred.

Pharmaceutical compositions of the invention comprise the above-described combination of components in the following ranges (w/w %); about 40–70%, preferably about 50–60% volatile solvent; about 5–50%, preferably about 20–35% fatty acid ester; about 2–60%, preferably about 2–30% essential oil; and an antihistaminic effective amount, i.e., about 5–30%, preferably 10–20% loratadine. The resulting pharmaceutical composition can be administered in any transdermally appropriate form, but a preferred method is to prepare a "reservoir type" patch which is applied to the skin and worn for a specific period of time to permit the penetration of a desired amount of loratadine through the skin. Most preferably, the patch of the invention will be worn for one to four days and provide a total daily dosage of about 0.5 to about 5 mg, preferably about 1 mg to about 3 mg of loratadine. The patch may then be replaced if necessary with a fresh patch, thereby providing a constant blood level of loratadine to the patient in need thereof. Preferably the reservoir of the patch contains a gel made from the above-described components in combination with a pharmaceutically acceptable thickener such as hydroxypropylcellulose or hydroxypropyl methylcellulose. Such a thickener is present in an amount (w/w %) of about 2 to about 4% of the pharmaceutical composition.

An example of a pharmaceutical composition of the present invention is as follows:

| LORATADINE GEL FORMULATION | |
|---|---|
| Component | Amount (mg/g) |
| Loratadine | 200 |
| Isopropyl Myristate | 250 |
| Rosemary oil | 20 |
| Hydroxypropyl cellulose | 20 |
| Ethanol | 510 |
| | 1000* |

*gel fill weight: 840 mg for a 15 cm$^2$ patch to contain 168 mg loratadine.

Dissolve the loratadine in the mixture of ethanol and isopropyl myristate. Add the rosemary oil and mix. Add the hydroxypropylcellulose and mix to prepare the gel.

Any suitable reservoir-type transdermal patch can be used to administer the preferred gel of the instant invention. For example, a closed reservoir patch can be manufactured comprising an impervious backing membrane such as a polyester/vinyl acetate membrane heat-sealed to a releasing membrane (i.e. a permeable membrane which controls the release of the active) such as a microporous polyethylene film with a reservoir between the membranes. The releasing membrane is advantageously coated with a pharmaceutically acceptable adhesive, such as an acrylate, silicone or rubber adhesive, e.g. a polyisobutylene adhesive, to adhere the patch to the skin of the host undergoing treatment. A release liner such as a polyester release liner can also be provided to cover the adhesive layer prior to application of the patch to the skin as is conventional in the art. This patch assembly can be packaged in an aluminum foil or other suitable pouch, again as is conventional in the art.

Alternatively, an open reservoir patch may be employed, which patch can comprise a porous membrane in place of the releasing membrane described above, or not include a membrane at all. An example of a porous membrane patch comprises a foil compartment with an adhesive border, a porous insert or membrane to hold the gel, and a foil release liner. A typical membrane-less patch comprises a foil compartment with an adhesive border, a peelable heat-sealed foil-based laminate upper backing member, and a secondary upper backing member of adhesive-coated non-woven polyester. Examples of membrane-less patches are those commercially available from MEDITECT and HILLTOP.

In vitro skin diffusion flux rates for the preferred formulation of the invention and for various loratadine formulations comprising only some of the preferred components are shown in Table I. The skin diffusion flux rates were obtained using human cadaver skin in a Franz diffusion cell. Flux is defined as the amount of drug that traverse skin over time for a specified area. In the table, IPM is used to abbreviate isopropyl myristate.

TABLE I
DIFFUSION DATA

| Vehicle | Flux (mg/15 cm$^2$/day) at appproximate steady state* |
|---|---|
| Final Gel (See example) | 2.26 |
| Final Gel w/o Rosemary oil | 0.87 |
| Loratadine and Ethanol | 0.18 |
| Loratadne, Ethanol and IPM | 0.66 |
| Loratadine, Ethanol and Rosemary oil | 0.09 |

*Average of at least 3 replicates from several skin donors.

It is of interest to the practice of the present invention that the total daily dosage of loratadine which is administered through the skin by the transdermal formulation may be less than the currently recommended clinical daily dose administered by the oral route. Moreover, it is anticipated that upon implementation of the invention the loratadine blood levels will be more consistent and controlled than those obtained upon oral administration of the drug. However, this is not a requirement of the invention. This feature is anticipated in view of clinical experience with other transdermal drugs. The particular dosage described above may be varied depending on the size and age of the patient and may also depend upon the severity of the condition being treated. Such dosage modification is within the skill of the clinical arts, and can be achieved, for example, by varying the concentration of active or by changing the size of the patch. The utilization of this new dosage form and its prescribed regimen will provide this efficacy of loratadine, having the advantages described above. Other frequencies of dosage application are anticipated, for example, a once every 3 day frequency or a once every 7 day frequency. Although a once-every 24 hours dosage regimen may be preferred, it is not intended that the invention be limited to any particular regimen.

The invention also contemplates a package or kit which contains a specific number of transdermal patches that may be utilized to complete a specified course of treatment. For example a package containing several patches would be utilized to complete a course of therapy, e.g. 7 24-hour patches for a seven day course of therapy.

We claim:

1. A transdermally acceptable pharmaceutical composition which comprises an anti-allergic effective amount of loratadine or its decarbalkoxylation product, about 40-70%, of a pharmaceutically acceptable volatile solvent, about 5-50%, of a fatty acid ester and about 2-60%, of an essential oil.

2. A composition of claim 1 comprising about 5-30%, of loratadine or its decarbalkoxylation product.

3. A composition of claim 2 wherein the volatile solvent is selected from methanol, ethanol, isopropanol, and cyclomethicone.

4. A composition of claim 2 wherein the fatty acid ester is selected from isopropyl myristate, isopropyl stearate, isopropyl palmitate, isopropyl isostearate and combinations thereof.

5. A composition of claim 2 wherein the essential oil is selected from rosemary oil, eucalyptus oil, spearmint oil, cedarwood oil, wintergreen oil and peppermint oil.

6. A composition of claim 2 comprising about 40-70% ethanol, about 5-50% isopropyl myristate, and about 2-60% rosemary oil.

7. A composition of claim 1 further comprising about 2-4% of a pharmaceutically acceptable thickener selected from hydroxypropylcellulose and hydroxypropyl methylcellulose.

8. A composition of claim 6 further comprising about 2-4% of a pharmaceutically acceptable thickener selected from hydroxypropylcellulose and hydoxypropyl methylcellulose.

9. A composition of claim 8 comprising 200 mg loratadine, 250 mg isopropyl myristate, 20 mg rosemary oil, 20 mg hydroxypropylcellulose and 510 mg ethanol.

10. A composition of claim 8 comprising 100 mg of the decarbalkoxylation product of loratadine, 250 mg of isopropyl myristate, 20 mg rosemary oil, 20 mg of hydroxypropylcellulose and 610 mg of ethanol.

11. The composition of claim 1 wherein 50 to 60% of a volatile solvent, 20-35% of a fatty acid ester and 2-30% of an essential oil and 10-20% loratadine or its decarboxylation product are employed.

12. A composition of claim 1 comprising about 10 to 20% of loratadine.

* * * * *